United States Patent
Kitazaki et al.

(10) Patent No.: US 6,297,421 B1
(45) Date of Patent: Oct. 2, 2001

(54) MEDICAL PRESSURE SENSITIVE ADHESIVE TAPE

(75) Inventors: Yasuaki Kitazaki; Fumio Tokumura, both of Tokyo (JP)

(73) Assignee: Nichiban Co., Ltd., Tokyo (JP)

( * ) Notice: Subject to any disclaimer, the term of this patent is extended or adjusted under 35 U.S.C. 154(b) by 0 days.

(21) Appl. No.: 09/622,936

(22) PCT Filed: Dec. 20, 1999

(86) PCT No.: PCT/JP99/07141

§ 371 Date: Aug. 24, 2000

§ 102(e) Date: Aug. 24, 2000

(87) PCT Pub. No.: WO00/40189

PCT Pub. Date: Jul. 13, 2000

(30) Foreign Application Priority Data

Dec. 28, 1998 (JP) .................................................. 10-371877

(51) Int. Cl.⁷ ........................................................ A61F 13/00
(52) U.S. Cl. ................................................ 602/42; 602/41
(58) Field of Search ........................................... 602/41–47

(56) References Cited

FOREIGN PATENT DOCUMENTS

| | | |
|---|---|---|
| 0628320 | 12/1994 | (EP) . |
| 39-4728 | 4/1939 | (JP) . |
| 2-1284 | 1/1990 | (JP) . |
| 6-13821 | 2/1994 | (JP) . |
| 6-256734 | 9/1994 | (JP) . |
| 6-343685 | 12/1994 | (JP) . |
| 7-48554 | 2/1995 | (JP) . |
| 7-022593 | 3/1995 | (JP) . |
| 0779064 | 6/1997 | (JP) . |
| 9-154933 | 6/1997 | (JP) . |

*Primary Examiner*—Michael A. Brown
*Assistant Examiner*—Laura M. Hamilton
(74) *Attorney, Agent, or Firm*—Dinsmore & Shohl LLP (57) ABSTRACT

A medical pressure sensitive adhesive tape includes a base material and a pressure sensitive adhesive layer formed on at least one side of the base material. The medical pressure sensitive adhesive tape is greatly lightened in skin irritation and has the following characteristics:

(a) the stress at 5% elongation being within a range of 0.1 to 8.0 N/24 mm as measured at a temperature of 23° C. and an extension rate of 100 mm/min;

(b) the viscosity (unit: Pa·s) of a pressure sensitive adhesive being within a range of 5.0 to 6.7 in terms of logarithm as determined from an initial slippage under shear load; and (c) the water-vapor transmission rate being within a range of 800 to 8,000 g/m²·24 hr as measured at a temperature of 40° C. and a relative humidity of 90%.

15 Claims, 1 Drawing Sheet

MEDICAL PRESSURE SENSITIVE ADHESIVE TAPE

TECHNICAL FIELD

The present invention relates to a medical pressure sensitive adhesive tape (including a sheet), and more particularly to a medical pressure sensitive adhesive tape suitable for use in fixing absorbent cotton, gauze, bandage, catheter, tube, poultice or the like to human skin in a medical field.

BACKGROUND ART

A medical pressure sensitive adhesive tape has a structure that a pressure sensitive adhesive layer is formed on at least one side of a base material. Since the medical pressure sensitive adhesive tape is intended to be applied to human skin, and often applied over a long period of time, it is designed after due consideration so as not to cause rash.

Specifically, as a base material of the medical pressure sensitive adhesive tape, is generally used a fabric, nonwoven fabric, plastic film, Japanese paper or the like having good flexibility and gas permeability. In order to prevent sweat generated by sweating from remaining in a site applied, a base material made of a material having excellent moisture permeability is also used. Further, a base material having good stretchability so as to permit conforming to the movement of human skin has been developed.

As a pressure sensitive adhesive for the medical pressure sensitive adhesive tape, a pressure sensitive adhesive such as the rubber, acrylic or silicone type, which neither exerts a sensitizing effect on skin nor causes marked skin irritation, is used. In order to prevent the occurrence of contact dermatitis by the adhesive tape, components constituting the pressure sensitive adhesive are generally selected from among raw materials that have borne good results and considered so as not to cause allergic dermatitis. In addition, the use of chemical substances strongly irritating the skin is avoided to the utmost to prevent the occurrence of dermatitis caused by a specific chemical substance.

The adhesive strength of the medical pressure sensitive adhesive tape is required to be sufficiently high to an extent that absorbent cotton, gauze, bandage, catheter, tube, poultice or the like can be fixed. On the other hand, the adhesive strength of the medical pressure sensitive adhesive tape is controlled so as to lower to an extend that the horny layer on skin surface is not markedly separated upon the peeling of the pressure sensitive adhesive tape, thereby avoiding causing rash.

As described above, the medical pressure sensitive adhesive tape is designed in vie of the kind of the base material, components of the pressure sensitive adhesive, level of adhesive strength, etc. in such a manner that it has moderate adhesive strength and moreover no rash is caused on the skin. However, the conventional medical pressure sensitive adhesive tapes have actually involved a problem that contact dermatitis such as rash is often caused on skin. It has also been difficult to balance the lightening of skin irritation with adhesive properties.

From the viewpoint of the skin irritation, the contact dermatitis by a medical pressure adhesive tape is generally such that erythema or papula attended with itch is caused on a site applied, unlike grave dermatitis spreading over a wide range, such as urusi (Japanese lacquer) poisoning. However, in an actual medical field, a medical pressure sensitive adhesive tape must be often applied over a long period of time or repeatedly many times on a specific site. In such a case, erythema or papula is worsened into blister, so that the epidermal part of the skin is in a damaged state. Namely, the patient comes to undergo a side effect attendant on treatment. In order to prevent such a side effect, it is necessary not to irritate the skin as much as possible. However, the conventional medical pressure sensitive tapes have been unable to cope with this requirement.

From the viewpoint of the adhesive properties, a necessary level for adhesive strength to human skin is determined by conducting practical experiments such as fixing of gauze. Accordingly, medical pressure sensitive adhesive tapes having adhesive strength to an extent that gauze or the like can be fixed to most persons without any problem under various service conditions have heretofore been developed and provided. However, the adhesive strength of a medical pressure sensitive adhesive tape to human skin may be often changed with time. For example, when the moisture permeability of the medical pressure sensitive adhesive tape is too low, sweat remains between the skin surface and the pressure sensitive adhesive layer when sweating occurs during sticking of the adhesive tape. As a result, the adhesive strength of the medical pressure sensitive adhesive tape is lowered with time, resulting in a failure to fix and hold gauze or the like.

In order to solve the above-described problem, it is only necessary to enhance the adhesive strength of the pressure sensitive adhesive so as to retain such adhesive strength that gauze or the like can be fixed even when sweating occurs. This method has been a general solving means from before. However, when the adhesive strength of the medical pressure sensitive adhesive tape is enhanced, such a medical pressure sensitive adhesive tape comes to have too high adhesive strength to the skin when no sweating occurs. As a result, a degree that the horny layer on the skin surface is simultaneously separated upon the peeling of the medical pressure sensitive adhesive tape is increased, so that dermatitis is liable to occur. In addition, when the adhesive strength of the pressure sensitive adhesive is enhanced with time, the pressure sensitive adhesive may remain on the skin surface upon the peeling of the medical pressure sensitive adhesive tape in some cases.

The above problem can be lightened to some extent by using a base material having excellent moisture permeability. However, the moisture permeability of a medical pressure sensitive adhesive tape not only depends on the moisture permeability of a base material, but also is greatly affected by the kind or the like of a pressure sensitive adhesive. When the moisture permeability of the pressure sensitive adhesive is low, the moisture permeability of the resulting medical pressure sensitive adhesive tape may become insufficient in some cases even when a base material having good moisture permeability is used. On the other hand, even when a pressure sensitive adhesive having good moisture permeability is used, or a method of making the structure of a pressure sensitive adhesive layer excellent in moisture permeability is adopted, it is difficult to balance the lightening of skin irritation with adhesive properties when the adhesive strength to human skin is insufficient, or the adhesive strength to human skin is decreased or increased with time, or cannot sufficiently conform to the extension and contraction of skin at a site applied.

The adhesive strength of a medical pressure sensitive adhesive tape can be objectively evaluated by, for example, measuring its adhesive strength to bakelite plate or stainless steel plate, whereby the composition and the like of a pressure sensitive adhesive can be adjusted so as to have moderate adhesive strength. However, this measured value of the adhesive strength does not stand in a simple proportional relationship to the adhesive strength when the medical pressure sensitive adhesive tape is actually applied to human skin. On the other hand, the adhesive strength of a medical pressure sensitive adhesive tape is measured by applying the adhesive tape to human skin, the adhesive strength varies with time, so that the adhesive strength often decreases or increases. The correlation between the physical properties of a pressure sensitive adhesive, such as adhesive strength, and skin irritation is also not said to have been sufficiently elucidated. Even from the viewpoint of controlling the physical properties of the pressure sensitive adhesive, such as adhesive strength, it has been a difficult problem to provide a medical pressure sensitive adhesive tape excellent in practical performance.

As described above, the mechanism of irritation given to human skin when a medical pressure sensitive adhesive tape is applied to the skin is not said to have been fully elucidated. In a medical field, it is strongly required to lighten the pain of a patient. Although it is important from the viewpoint of providing a medical pressure sensitive adhesive tape excellent in practical performance that the material and form of a base material, the composition and adhesive properties of a pressure sensitive adhesive, etc. are suitably selected and combined with each other, there is a demand for planning to provide a medical pressure sensitive adhesive tape balanced between the lightening of skin irritation and adhesive properties at a high level by approaching the mechanism of skin irritation from a new point of view.

DISCLOSURE OF THE INVENTION

It is an object of the present invention to provide a medical pressure sensitive adhesive tape in which skin irritation is greatly lightened, and its adhesive strength to skin is stably retained at a moderate level over a long period of time.

As described above, a pressure sensitive adhesive used in a field of medical pressure sensitive adhesive tapes does generally not contain such a component that allergic dermatitis or dermatitis caused by a chemical substance is caused. Accordingly, it can be considered that the cause of contact dermatitis is not attributed to a specific component contained in the pressure sensitive adhesive. Therefore, the present inventors have carried out a detailed investigation as to the developmental situation of contact dermatitis caused when a medical pressure sensitive adhesive tape is applied to human skin and made an effort to elucidate the mechanism of skin irritation. As a result, the following facts have become clear.

(1) A horny layer on skin surface is separated when a medical pressure sensitive adhesive tape is applied to human skin and then peeled, so that inflammation is caused on the epidermis or dermis under the horny layer.

(2) Since a base material of the medical pressure sensitive adhesive tape is hard compared with the skin, the extension and contraction of the skin at a site applied is restrained, so that a stress is built up in the applied site to cause inflammation is caused.

(3) Since the width of the medical pressure sensitive adhesive tape is not sufficient when the medical pressure sensitive adhesive tape is applied to the skin to hold and fix gauze or the like to the skin, the adhesive strength necessary to hold and fixing it is concentrated at the applied site having a narrow area, so that inflammation is caused.

(4) Since the viscosity of the pressure sensitive adhesive is high, the pressure sensitive adhesive cannot conform to the extension and contraction of the skin at the applied site, and a stress is concentrated at the applied site by a portion that cannot conform, so that inflammation is caused.

(5) Since the moisture permeability of the medical pressure sensitive adhesive tape is not sufficient, sweat is built up at the applied site. As a result, a film of water is formed between the pressure sensitive adhesive layer and the skin surface, so that the adhesive strength of the medical pressure sensitive adhesive tape to the skin is lowered. In addition, when the moisture permeability of the medical pressure sensitive adhesive tape is too low, the cause of separation of horny layer upon its peeling, and dermal diseases such as rash, itch and erythema is formed.

These observation results have been synthetically judged to forward a further investigation. As a result, it has been found that the above object can be achieved by controlling the stress of a pressure sensitive adhesive tape upon its extension as determined under specific conditions, the viscosity property of a pressure sensitive adhesive as determined under specific conditions, and the moisture permeability of the pressure sensitive adhesive tape within respective specified, selected ranges. The medical pressure sensitive adhesive tape according to the present invention can exhibit excellent various performance characteristics that (i) skin irritation is greatly lightened, (ii) the retention of water by sweating is extremely little, (iii) the adhesive strength to human skin is stably retained at a moderate level from the initial stage up to after applied for a long period of time, (iv) neither slippage nor falling occurs in a test for practical use that gauze or the like is fixed, and (v) no pressure sensitive adhesive remains on the skin after peeling of the adhesive tape. The present invention has been led to completion on the basis of these findings.

According to the present invention, there is thus provided a medical pressure sensitive adhesive tape comprising a base material and a pressure sensitive adhesive layer formed on at least one side of the base material, wherein the adhesive tape has the following characteristics:

(a) the stress at 5% elongation being within a range of 0.1 to 8.0 N/24 mm as measured at a temperature of 23° C. and an extension rate of 100 mm/min;

(b) the viscosity (unit: Pa·s) of a pressure sensitive adhesive being within a range of 5.0 to 6.7 in terms of logarithm as determined from an initial slippage under shear load; and (c) the water-vapor transmission rate being within a range of 800 to 8,000 g/m$^2$·24 hr as measured at a temperature of 40° C. and a relative humidity of 90%.

BRIEF DESCRIPTION OF THE DRAWING

The present invention may be further understood in view of the drawing which schematically shows a medical pressure sensitive adhesive tape 10 comprisig a base material 20 and a pressure sensitive adhesive layer 30 formed on least one side of the base material 20. The relative thicknesses of the layers set forth in the drawing is not limiting of the invention disclosed herein.

BEST MODE FOR CARRYING OUT THE INVENTION

Figure 1:
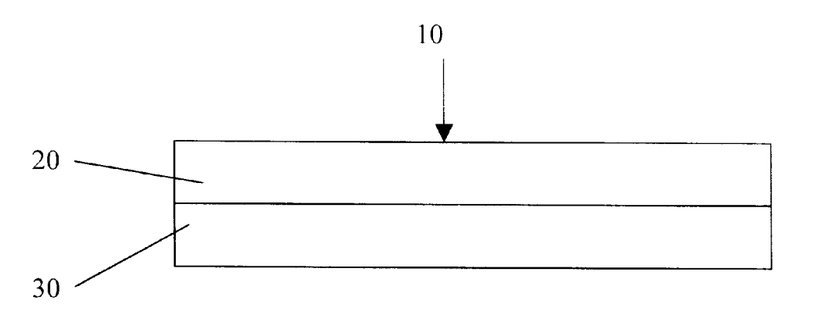

The medical pressure sensitive adhesive tape according to the present invention is required to have a stress at 5% elongation within a range of 0.1 to 8.0 N/24 mm as measured at a temperature of 23° C. and an extension rate of 100 mm/min. Such property can be mainly achieved by selecting a base material.

In the present invention, a fabric, a nonwoven fabric, a film, a perforated film or a composite material thereof may be used as the base material. The film is preferably a microporous, air-permeable film. The base material is desirably excellent in air permeability and moisture permeability, and it has been proved that the stress at 5% elongation is extremely important from the viewpoint of contact dermatitis such as rash.

When a medical pressure sensitive adhesive tape is applied to human skin, a proportion of deformation by extension and contraction incurred with the distortion of the skin by movement or the like is about ±5%. More specifically, the medical pressure sensitive adhesive tape often undergoes deformation by extension and contraction to an extent of about ±5% upon its application. Since the medical pressure sensitive adhesive tape is generally prepared by using a flexible base material, it is easily deformed upon contraction of the skin. On the other hand, when the stress upon extension of the medical pressure sensitive adhesive tape is too high, the extension of the skin is restrained at the applied site. As a result, the stress is built up at the applied site, and inflammation is easy to be caused. Accordingly, as the stress applied at the time the medical pressure sensitive adhesive tape is extended at ordinary temperature (23° C.) and an ordinary moving rate becomes as low as possible, a lower stress is applied to the applied site of the skin.

However, when the stress upon the extension is too low, the base material becomes limp, and the adhesive tape becomes hard to handle. Therefore, it has been proved that the stress of the medical pressure sensitive adhesive tape at the time it is extended by 5% at a temperature of 23° C. and a rate of 100 mm/min must be at least 0.1 N/24 mm. If the stress upon extension exceeds 8.0 N/24 mm, the conformability to the distortion of the skin is lowered to give a too high stress to the applied site of the skin. The stress at 5% elongation is controlled within a suitable range, thereby avoiding applying an excessive stress to the skin at the applied site even when the adhesive strength is concentrated at the narrow applied site. The stress at 5% elongation is preferably of the order of 0.2 to 7.5 N/24 mm.

In the medical pressure sensitive adhesive tape according to the present invention, a silicone pressure sensitive adhesive, rubber pressure sensitive adhesive, acrylic pressure sensitive adhesive, hydrogel pressure sensitive adhesive or the like may be used as the pressure sensitive adhesive. In the medical pressure sensitive adhesive tape according to the present invention, it is necessary that the viscosity (unit: Pa·s) of the pressure sensitive adhesive is within a range of 5.0 to 6.7 in terms of logarithm (common logarithm) as determined from an initial slippage under shear load.

If the viscosity of the pressure sensitive adhesive is too high, the pressure sensitive adhesive layer cannot conform to the extension and contraction of the skin at the applied site, and a stress is concentrated at the applied site by a portion that cannot conform, so that inflammation is caused. The present inventors have carried out an investigation as to the correlation between the viscosity of the pressure sensitive adhesive forming the pressure sensitive adhesive layer and skin irritation. As a result, it has been found that the conformability of the pressure sensitive adhesive layer to the skin can be greatly improved by controlling the logarithm of the viscosity of the pressure sensitive adhesive as determined from an initial slippage under shear load within a limited specific range.

If the logarithm of the viscosity of the pressure sensitive adhesive is smaller than 5.0, the pressure sensitive adhesive remains on the skin upon peeling of the resulting medical pressure sensitive adhesive tape from the skin, or the adhesive tape is liable to slip from a prescribed position during its sticking because the pressure sensitive adhesive is too soft though the initial adhesive strength of the medical pressure sensitive adhesive tape to the skin is improved. When this slippage becomes marked, the medical pressure sensitive adhesive tape fails to surely fix and hold gauze, catheter, tube or the like to skin surface. If the logarithm of the viscosity of the pressure sensitive adhesive exceeds 6.7, the pressure sensitive adhesive is too hard, and the conformability of a pressure sensitive adhesive layer formed from such a pressure sensitive adhesive to the extension and contraction of the skin is lowered. Accordingly, a stress is given to the skin at the applied site with the extension and contraction of the skin, so that skin irritation is increased. The logarithm of the viscosity of the pressure sensitive adhesive is preferably 5.5 to 6.5.

As described above, in the medical pressure sensitive adhesive tape according to the present invention, the stress at 5% elongation and the logarithm of the viscosity of the pressure sensitive adhesive are controlled within the respective specified, limited ranges, whereby the stress against the skin is reduced to a great extent to lighten skin irritation, and moreover the balance between lightening of skin irritation, and easy use, adhesive properties and the like is made good.

The medical pressure sensitive adhesive tape according to the present invention is required to have a water-vapor transmission rate within a range of 800 to 8,000 g/m$^2$·24 hr as measured at a temperature of 40° C. and a relative humidity of 90%. A medical pressure sensitive adhesive tape desirably has a water-vapor transmission rate higher than the amount of sweat from the skin. The amount of sweat from human skin in a calm state is about 700 to 900 g/m$^2$·24 hr in average though there is a difference among individuals according to age, sex and the like, and increases or decreases by changes in the quantity of motion and temperature. When sweat generated by sweating remains between a medical pressure sensitive adhesive tape applied and skin surface, a film of water is formed between the pressure sensitive adhesive layer and the skin surface, so that the adhesive strength of the adhesive tape to the skin is lowered. When the adhesive strength to the skin is lowered, the ability of the medical pressure sensitive adhesive tape to fix and hold gauze, tube or the like is lowered. Therefore, it is desirable from the viewpoint of retaining a good adhesive state that water brought to the skin surface by sweating be immediately vaporized into the air through the medical pressure sensitive adhesive tape.

When the water-vapor transmission rate of the medical pressure sensitive adhesive tape is too low, water generated by sweating is liable to remain on the skin surface. In addition, when the water-vapor transmission rate of the medical pressure sensitive adhesive tape is too low, the cause of separation of horny layer upon its peeling, and dermal diseases such as rash, itch and erythema is formed. About 8,000 g/m$^2$·24 hr suffices the upper limit of the water-vapor transmission rate from the viewpoint of practical use. The water-vapor transmission rate is often about 1,000 to 7,000 g/m$^2$·24 hr.

In the present invention, the stress at 5% elongation, logarithm of the viscosity of an pressure sensitive adhesive and water-vapor transmission rate are selected so as to fall within respective specified ranges, and combined with one another, thereby permitting the provision of a medical pressure sensitive adhesive tape which can exhibit such excellent various performance characteristics that (1) skin irritation is markedly lightened,
(2) the retention of water by sweating is extremely little,
(3) the adhesive strength to human skin is stably retained at a moderate level from the initial stage of application up to after applied for a long period of time,
(4) neither slippage nor falling occurs in a practical test that gauze or the like is fixed, and
(5) no pressure sensitive adhesive remains on the skin after peeling of the adhesive tape.

The adhesive strength of the medical pressure sensitive adhesive tape according to the present invention is of the order of generally 0.6 to 10.0 N/24 mm, preferably 1.0 to 9.0 N/24 mm in terms of the adhesive strength of a pressure sensitive adhesive tape 24 mm in width to a bakelite panel as measured in accordance with the 180 degree peeling method prescribed in JIS Z 0237. If the adhesive strength to bakelite panel is too low, the adhesive strength is insufficient for human skin, thereby making it difficult to fix gauze or the like. If the adhesive strength to bakelite panel is too high, disadvantages such as separation of horny layer are easy to occur.

The adhesive strength of the medical pressure sensitive adhesive tape according to the present invention to human skin is of the order of generally 0.5 to 5.0 N/24 mm, preferably 0.6 to 4.0 N/24 mm as defined by adhesive strength to the sink of a human inner lower arm. If the adhesive strength to the human skin is too low, it is difficult to stably fix absorbent cotton, gauze, bandage, catheter, tube, poultice or the like to human skin. If the adhesive strength to the human skin is too high, the horny layer at a site applied is markedly separated upon peeling of the medical pressure sensitive adhesive tape. In the medical pressure sensitive adhesive according to the present invention, conformability to skin, moisture permeability, viscosity of the pressure sensitive adhesive and the like are balanced with one another within the respective preferred ranges, so that the adhesive strength to human skin is extremely stable from the initial stage of application to a skin surface up to after applied for a long period of time, so that marked increase or decrease in adhesive strength is not caused, and no pressure sensitive adhesive remain on the skin surface after peeling of the adhesive tape.

In the medical pressure sensitive adhesive tape according to the present invention, may be used silicone pressure sensitive adhesives, rubber pressure sensitive adhesives, acrylic pressure sensitive adhesives, hydrogel pressure sensitive adhesives and the like. Among these pressure sensitive adhesives, acrylic pressure sensitive adhesives obtained by (co)polymerizing a monomer or monomer mixture comprising an alkyl (meth)acrylate as a main monomer are preferred. As the acrylic pressure sensitive adhesives, may be mentioned copolymers of an alkyl (meth)acrylate and a functional monomer and/or vinyl ester monomer copolymerizable therewith.

The alkyl (meth)acrylate preferably has 4 to 12 carbon atoms. The functional monomer is used in a proportion of generally 0 to 30 wt. %, preferably 1 to 10 wt. %. Specific examples of the functional monomer include acrylic acid, methacrylic acid and 2-hydroxyethylacrylic acid. The vinyl monomer is used in a proportion of generally 0 to 40 wt. %, preferably 2 to 30 wt. %. Specific examples of the vinyl monomer include vinyl acetate, vinyl formate and vinyl laurate.

Acrylic pressure sensitive adhesives comprising, as an adhesive component, an acrylic copolymer obtained by using an alkoxypolyalkylene glycol (meth)acrylate and a hydroxyl group- or carboxyl group-containing monomer as comonomers in combination are particularly preferred from the viewpoint of stable tackiness to skin, high moisture permeability, lessening of corneum separation and lightening of pain in the skin upon peeling.

More specifically, as preferable acrylic pressure sensitive adhesives, may be mentioned copolymers of (A) 50 to 97.5 wt. %, preferably 70 to 95 wt. % of an alkyl (meth)acrylate having an alkyl group having 4 to 12 carbon atoms, (B) 2 to 49.5 wt. %, preferably 4 to 29 wt. % of an alkoxypolyalkylene glycol (meth)acrylate, and (C) 0.5 to 15 wt. %, preferably 1 to 10 wt. % of a hydroxyl group- or carboxyl group-containing monomer. The copolymers may be those obtained by copolymerizing (D) a still further copolymerizable vinyl monomer within a range of about 0 to 30 wt. %.

As examples of the alkyl (meth)acrylate having an alkyl group having 4 to 12 carbon atoms, may be mentioned n-butyl acrylate, isobutyl acrylate, t-butyl acrylate, 2-ethylhexyl acrylate, n-octyl acrylate, isooctyl acrylate, isononyl acrylate, decyl acrylate, dodecyl acrylate, n-butyl methacrylate, isobutyl methacrylate, t-butyl methacrylate, 2-ethylhexyl methacrylate, n-octyl methacrylate, isooctyl methacrylate, isononyl methacrylate, decyl methacrylate and dodecyl methacrylate. Among these, 2-ethylhexyl acrylate, n-octyl acrylate, isooctyl acrylate and isononyl acrylate are preferred. These alkyl (meth)acrylates may be used either singly or in any combination thereof.

The alkoxypolyalkylene glycol (meth)acrylate is a (meth) acrylic ester represented by the following formula (1):

(1)

wherein $R_1$ and $R_2$ are independently a hydrogen atom or a methyl group, $R_3$ is an alkyl group having 1 to 20 carbon atoms, and n is an integer of 2 to 12.

Specific examples of the monomer represented by the formula (1) include methoxydiethylene glycol acrylate ($R_1$=H, $R_2$=H, $R_3$=CH$_3$, n=2), methoxydiethylene glycol methacrylate ($R_1$=CH$_3$, $R_2$=H, $R_3$=CH$_3$, n=2), methoxydipropylene glycol acrylate ($R_1$=H, $R_2$=CH$_3$, $R_3$=CH$_3$, n=2), methoxydipropylene glycol methacrylate ($R_1$=CH$_3$, $R_2$=CH$_3$, $R_3$=CH$_3$, n=2), ethoxydiethylene glycol acrylate ($R_1$=H, $R_2$=H, $R_3$=C$_2$H$_5$, n=2), ethoxydiethylene glycol methacrylate ($R_1$=CH$_3$, $R_2$=H, $R_3$=C$_2$H$_5$, n=2), ethoxydipropylene glycol acrylate ($R_1$=H, $R_2$=CH$_3$, $R_3$=C$_2$H$_5$, n=2), ethoxydipropylene glycol methacrylate ($R_1$=CH$_3$, $R_2$=CH$_3$, $R_3$=C$_2$H$_5$, n=2), methoxytriethylene glycol acrylate ($R_1$=H, $R_2$=H, $R_3$=CH$_3$, n=3), methoxytriethylene glycol methacrylate ($R_1$=CH$_3$, $R_2$=H, $R_3$=CH$_3$, n=3), methoxytripropylene glycol acrylate ($R_1$=H, $R_2$=CH$_3$, $R_3$=CH$_3$, n=3), methoxytripropylene glycol methacrylate ($R_1$=CH$_3$, $R_2$=CH$_3$, $R_3$=C$_2$H$_5$, n=3), methoxypolyethylene glycol acrylate ($R_1$=H, $R_2$=H, $R_3$=CH$_3$, n=4 to 10), methoxypolyethylene glycol methacrylate ($R_1$=CH$_3$, $R_2$=H, $R_3$=CH$_3$, n=4 to 10), methoxypolypropylene glycol acrylate ($R_1$=H, $R_2$=CH$_3$, $R_3$=CH$_3$, n=4 to 10) and methoxypolypropylene glycol methacrylate ($R_1$=CH$_3$, $R_2$=CH$_3$, $R_3$=CH$_3$, n=4 to 10).

As examples of the hydroxyl group- or carboxyl group-containing monomer, may be mentioned hydroxyalkyl (meth)acrylates and carboxyalkyl (meth)acrylates. Specific examples of these monomers include 2-hydroxyethyl acrylate, 2-carboxyethyl acrylate, 2-hydroxypropyl acrylate, 2-carboxypropyl acrylate, 3-hydroxypropyl acrylate, 3carboxypropyl acrylate, 4-hydroxybutyl acrylate, 4-carboxybutyl acrylate, 2-hydroxyethyl methacrylate, 2-carboxyethyl methacrylate, 2-hydroxypropyl methacrylate, 2-carboxypropyl methacrylate, 3-hydroxypropyl methacrylate, 3-carboxypropyl methacrylate, 4-hydroxybutyl methacrylate and 4-carboxybutyl methacrylate.

As examples of the hydroxyl group-containing monomer, may be mentioned hydroxyl group-containing (meth)acrylic esters represented by the formula (2):

(2)

wherein $R_4$ and $R_5$ are independently a hydrogen atom or a methyl group, and m is an integer of 2 to 12, such as polyethylene glycol (meth)acrylates and polypropylene glycol (meth)acrylates.

As examples of the carboxyl group-containing monomer, may be mentioned carboxyl group-containing (meth)acrylic esters represented by the formula (3):

(3)

wherein $R_6$ is a hydrogen atom or a methyl group, and X is a divalent organic group having at least 2 carbon atoms and may contain a heteroatom such as an oxygen, nitrogen or sulfur atom.

In the formula (3), the number of carbon atoms in X is preferably 2 to 50, more preferably 2 to 30. The heteroatom is an oxygen atom in many cases. As specific examples of X, may be mentioned linear or branched alkylene groups having at least two carbon atoms, $-R_7-OCO-R_8-$ (wherein $R_7$ and $R_8$ are alkylene groups) and $-R_9-OCO-R_{10}-OCO-R_{11}-$ (wherein $R_9$, $R_{10}$ and $R_{11}$ are alkylene groups). Specific examples of the carboxyl group-containing (meth)acrylic esters represented by the formula (3) include 2-carboxyethyl acrylate, 2-acryloyloxyethyl-succinic acid and ω-carboxypolycaprolactone acrylate.

As examples of the still further copolymerizable vinyl monomer, may be mentioned alkyl (meth)acrylates such as methyl acrylate, ethyl acrylate, isopropyl acrylate, methyl methacrylate, ethyl methacrylate, isopropyl methacrylate, tridecyl acrylate and tridecyl methacrylate; carboxyl group-containing monomers such as acrylic acid, methacrylic acid, maleic acid, maleic anhydride and itaconic acid; (meth) acrylamides and derivatives thereof such as acrylamide, methacrylamide and N-methylolacrylamide; epoxy group-containing monomers such as glycidyl acrylate and glycidyl methacrylate; vinyl esters such as vinyl acetate; unsaturated nitrites such as acrylonitrile and methacrylonitrile; and vinyl aromatic compounds such as styrene.

To the pressure sensitive adhesives used in the present invention, may be added general-purpose various additives if desired. When the moisture permeability and air permeability of the pressure sensitive adhesive such as an acrylic pressure sensitive adhesive are insufficient, minute bubbles may be contained in the pressure sensitive adhesive in a step of forming a pressure sensitive adhesive layer. Examples of a method for containing the minute bubbles in the pressure sensitive adhesive layer include (1) a method in which a solution of a pressure sensitive adhesive is applied to a base material or separator, and the pressure sensitive adhesive is then caused to bubble by presetting a temperature, at which the solvent is heated and dried, to a higher temperature than usual, (2) a method in which a solution of a pressure sensitive adhesive is applied to the surface of a release sheet to form a pressure sensitive adhesive layer, droplets of water having a droplet diameter of 10 to 100 μm are sprayed on the surface of the pressure sensitive adhesive layer while the pressure sensitive adhesive layer is in an undried state, and the pressure sensitive adhesive layer is then dried to transfer it to an air-permeable adhesive tape (Japanese Patent Publication No. 22593/1995), and (3) a method in which a solution of a pressure sensitive adhesive is applied to the surface of release paper and dried at 40 to 65° C. to laminate a nonwoven fabric thereon at the time the solution has become a semi-dried state, the laminate is heated and dried again, and lastly the solvent is fully evaporated at about 95° C. (Japanese Patent Publication No. 4728/1964).

The medical pressure sensitive adhesive tape according to the present invention can be produced by applying a pressure sensitive adhesive to at least one side of a flexible base material in accordance with a method known per se in the art. The pressure sensitive adhesive may be applied to a separator to transfer it to the base material. In order to apply the pressure sensitive adhesive, it is only necessary to apply a solution with a base polymer and optional additive ingredients uniformly dissolved or dispersed in an organic solvent to the base material or separator and dry it. No particular limitation is imposed on the thickness of the pressure sensitive adhesive layer. However, it is of the order of generally 20 to 100 μm, preferably 30 to 70 μm.

EXAMPLES

The present invention will hereinafter be described specifically by the following Examples. Incidentally. all designations of "part" or "parts" and "%" as will be used in the following examples and comparative examples mean part or parts by weight and % by weight unless expressly noted.

Physical properties and performance of pressure sensitive adhesive tapes were determined in accordance with the following respective methods:

(1) Adhesive Strength to Bakelite Panel:

The adhesive strength of each pressure sensitive adhesive tape 24 mm in width to a bakelite panel was measured in accordance with the 180 degree peeling method prescribed JIS Z 0237.

(2) Logarithm of Viscosity of Pressure Sensitive Adhesive:

The logarithm is a common logarithm of a viscosity (unit: Pa·s) of each pressure sensitive adhesive as determined from an initial value of shear slippage and determined in accordance with the following method.

A solution of each pressure sensitive adhesive is applied to one side of a polyester film (Lumirror #25, trade name, product of Toray Industries, Inc.) having a thickness of 25 μm so as to give a dry coating thickness of L [μm], and the polyester film is then cut into pieces 12 mm×50 mm in size to prepare a sample. After this sample is stuck at a sticking area of 12 mm×20 mm on a glass sheet stood vertically to adapt itself to the measuring surroundings (temperature: 23° C.; relative humidity: 65%), a load of 200 g is applied to the lower side of the sample to read a slippage of the upper side every 5 minutes by means of a reading microscope. A degree X [mm] of slippage per hour is calculated out from an initial linear relationship. The viscosity (V) of the pressure sensitive adhesive found from the initial slippage may be calculated out in accordance with the following equation:

$$V = [(200 \times 980)/(1.2) \times 2.0)/(0.1X/3600) \times (L/10000)$$
$$= 294000 \times L/X \text{ (poise)}$$
$$= 29400 \times L/X \text{ (Pa·s)}$$

Since the measured value was great in figure, its common logarithm was calculated out.

(3) Tensile Stress at 5% Elongation of Pressure Sensitive Adhesive Tape:

A stress (sample width: 24 mm; crosshead interval: 100 mm) at 5% elongation of a sample was measured at 23° C. and a crosshead speed of 100 mm/min by means of a tensile tester in accordance with JIS K 7115.

(4) Water-vapor Transmission Rate of Pressure Sensitive Adhesive Tape:

The water-vapor transmission rate of each pressure sensitive adhesive tape was measured at a temperature of 40° C. and a relative humidity of 90% according to the conditions B prescribed in JIS Z 0208. Specifically, one side of the sample was adjusted at a temperature of 40° C. and a relative humidity of 90%, and about 16 g of a moisture absorbent (calcium chloride) were placed on another side to cause moisture passed through the sample to be absorbed, whereby a weight change of the moisture absorbent was converted into a value per 1 m$^2$ and 24 hours to regard its value as a water-vapor transmission rate (n=3).

(5) Adhesive Strength to Human Skin:

Two strips of each pressure sensitive adhesive tape of 24 mm×70 mm were stuck in a transverse direction on inner lower arms of 8 adult men. The adhesive strength to the skin was measured at a peeling angle of 90° by means of an Instron tensile tester after 1 hour (initial) and 24 hours from the sticking.

(6) Conductance:

Two strips of each pressure sensitive adhesive tape of 24 mm×70 mm were stuck in a transverse direction on inner lower arms of 8 adult men. After 1 hour (initial) and 24 hours from the sticking, the electric conductance of the epidermal horny layer was measured by passing a high-frequency current of 3.5 MHz by means of SKICON 200 (manufactured by IBS K.K.). Since the conductance is correlated with water content, it is used as an index to a quantity of water retained on the skin surface (n=8).

(7) Skin Irritation:

Two strips of each pressure sensitive adhesive tape of 24 mm×70 mm were stuck in a transverse direction on inner lower arms of 8 adult men. Skin irritation by the pressure sensitive adhesive tape at central and edge portions of a site applied was evaluated after 24 hours from the sticking in accordance with the Japanese standard (n=8).

The Japanese standard is a standard prescribed by the Japanese patch test research group. More specifically, weights of 0, 0.5, 1, 2, 3 and 4 points were given to the following standard, −, ±, +, ++, +++ and ++++, respectively, to multiply an average value of the evaluation results of the respective subjects by 100 to express the value thereof as an skin irritation index.

Criterion

−: Not reacted,
±: Light erythema,
+: Erythema,
++: Erythema+edema,
+++: Erythema+edema+papule,
++++: Erythema+edema+papule, serous papule, vesicle.

Numerical values of about 10, about 30 and at least 50 mean that irritation is little, that irritation is strong, and that irritation is heavy, respectively.

(8) Test for Practical use:

Gauze of 8 layers one over another having a size of 30 mm×30 mm was fixed for 24 hours to each of inner lower arms of 8 adult men by means of each pressure sensitive adhesive tape of 24 mm×70 mm. After 24 hours, a state of the pressure sensitive adhesive tape stuck was observed to evaluate the adhesive tape as to practical use in accordance with the following standard (n=8):

○: Normal;

Δ: Partial separation or slippage occurred;

×: Marked slippage or falling occurred.

Example 1

A monomer mixture was radical-polymerized in a mixed solvent of ethyl acetate and acetone in accordance with a method known per se in the art, thereby obtaining a terpolymer of 2-ethylhexyl acrylate/methoxynonaethylene glycol acrylate/nonaethylene glycol methacrylate (83 parts/16 parts/1 part). To 100 parts (solid content) of the terpolymer thus obtained, were added 0.6 parts of a polyisocyanate crosslinking agent (Koronate L, product of Nippon Polyurethane Industry Co., Ltd.) as a crosslinking agent. The resultant mixture was fully stirred to prepare a solution of Acrylic Pressure Sensitive Adhesive (A).

This pressure sensitive adhesive solution was applied to a separator having a thickness of 120 μm, one surface of which had been subjected to a silicone treatment, so as to give a dry coating thickness of 40 μm, and heated and dried at 120° C. for 5 minutes. An air-permeable polyolefin film having a thickness of 90 μm was used as a base material to uniformly press-bond it to the surface of the dry pressure sensitive adhesive layer, thereby obtaining a pressure sensitive adhesive tape. The pressure sensitive adhesive tape was further aged at 50° C. for 7 days to produce a medical pressure sensitive adhesive tape.

This medical pressure sensitive adhesive tape was cut into pieces having a width of 24 mm to conduct various tests. The results thereof are shown in Table 1. This medical pressure sensitive adhesive tape was found to be an excellent medical pressure sensitive adhesive tape in that skin irritation was scarcely caused at both edge and central portions of a site applied, there was no abnormality even in the test for practical use that gauze was fixed.

Comparative Example 1

A solution of Pressure Sensitive Adhesive (A) prepared in accordance with the same procedure as in Example 1 was applied to a separator having a thickness of 120 μm, one surface of which had been subjected to a silicone treatment, so as to give a dry coating thickness of 40 μm, and heated and dried at 120° C. for 5 minutes. A high density polyethylene film (subjected to corona treatment on one side thereof) having a thickness of 130 μm was used as a base material to uniformly press-bond the corona treated surface to the surface of the dry pressure sensitive adhesive layer, thereby obtaining a pressure sensitive adhesive tape. The pressure sensitive adhesive tape was further aged at 50° C. for 7 days to produce a medical pressure sensitive adhesive tape. This medical pressure sensitive adhesive tape was cut into pieces having a width of 24 mm to conduct various tests. The results thereof are shown in Table 1.

In this medical pressure sensitive adhesive tape, skin irritation was only slightly caused at both edge and central portions of a site applied, but marked separation occurred in the test for practical use, and the gauze fixed slipped after 24 hours as if it fell off. The conductance on the skin surface after 24 hours from the sticking markedly increased. It is therefore considered that since sweat remained between the pressure sensitive adhesive layer and the skin surface, the adhesive strength of the pressure sensitive adhesive layer to the skin surface was decreased. The adhesive strength of this pressure sensitive adhesive tape to human skin was sufficient in initial value, but was markedly reduced after 24 hours. Since the moisture permeability of this pressure sensitive adhesive tape was as low as 34 g/(m²·24 hr), it is considered that retention of sweat with time was marked.

Example 2

A monomer mixture was radical-polymerized in a mixed solvent of ethyl acetate and acetone in accordance with a method known per se in the art, thereby obtaining a terpolymer of 2-ethylhexyl acrylate/vinyl acetate/acrylic acid (83 parts/15 parts/2 parts). To 100 parts (solid content) of the terpolymer thus obtained, were added 0.6 parts of a polyisocyanate crosslinking agent (Koronate L, product of Nippon Polyurethane Industry Co., Ltd.). The resultant mixture was fully stirred to prepare a solution of Acrylic Pressure Sensitive Adhesive (B).

This pressure sensitive adhesive solution was applied to a separator having a thickness of 120 μm, one surface of which had been subjected to a silicone treatment, so as to give a dry coating thickness of 60 μm, and heated and dried at 150° C. for 8 minutes. Minute bubbles were generated in the pressure sensitive adhesive by this treatment. A knitted fabric of cotton yarn was used as a base material to press-bond it to the surface of the dry pressure sensitive adhesive layer so as not to wrinkle, thereby obtaining a pressure sensitive adhesive tape. The pressure sensitive adhesive tape was further aged at 50° C. for 7 days to produce a medical pressure sensitive adhesive tape. This medical pressure sensitive adhesive tape was cut into pieces having a width of 24 mm to conduct various tests. The results thereof are shown in Table 1.

This medical pressure sensitive adhesive tape scarcely underwent skin irritation at both edge and central portions of a site applied and exhibited good holding and fixing function even in the test for practical use. It is understood that the water-vapor transmission rate can be heightened by bubbling the pressure sensitive adhesive layer. The conductance after 24 hours is scarcely varied by this treatment compared with the initial value.

Comparative Example 2

A solution of Pressure Sensitive Adhesive (B) prepared in accordance with the same procedure as in Example 2 was applied to a separator having a thickness of 120 μm, one surface of which had been subjected to a silicone treatment, so as to give a dry coating thickness of 60 μm, and heated and dried at 120° C. for 5 minutes. A plain cotton fabric was used as a base material to press-bond it to the surface of the dry pressure sensitive adhesive layer so as not to wrinkle, thereby obtaining a pressure sensitive adhesive tape. The pressure sensitive adhesive tape was further aged at 50° C. for 7 days to produce a medical pressure sensitive adhesive tape. This medical pressure sensitive adhesive tape was cut into pieces having a width of 24 mm to conduct various tests. The results thereof are shown in Table 1.

This medical pressure sensitive adhesive tape showed a high value as to skin irritation at a central portion of a site applied and a higher value at an edge portion. In the test for practical use, good holding and fixing ability was exhibited. As apparent from the fact that the adhesive strength to bakelite panel was high, this is judged to be due to high adhesive strength inherent in the pressure sensitive adhesive. The fact that in skin irritation, strong irritation occurred at the edge portion in particular is considered to be due to the fact that since the stress at 5% elongation of the pressure sensitive adhesive tape is as high as 160.8 N/24 mm that is about 500 times as high as Example 2, the conformability to skin was extremely poor. The adhesive strength to human skin was considerably lowered after 24 hours compared with the initial value because the water-vapor transmission rate was low. The fact that the retention of water between the pressure sensitive adhesive layer and the skin surface was increased can be known by marked increase in the conductance after 24 hours.

Example 3

A monomer mixture was radical-polymerized in a mixed solvent of ethyl acetate and acetone in accordance with a method known per se in the art, thereby obtaining a copolymer of 2-ethylhexyl acrylate/acrylic acid (96 parts/4 parts). To 100 parts (solid content) of the copolymer thus obtained, were added 0.6 parts of a polyisocyanate crosslinking agent (Koronate L, product of Nippon Polyurethane Industry Co., Ltd.). The resultant mixture was fully stirred to prepare a solution of Acrylic Pressure Sensitive Adhesive (C).

This pressure sensitive adhesive solution was applied to a separator having a thickness of 120 μm, one surface of which had been subjected to a silicone treatment, so as to give a dry coating thickness of 50 μm, and heated and dried at 150° C. for 8 minutes. Minute bubbles were generated in the pressure sensitive adhesive by this treatment. A nonwoven urethane fabric having a basis weight of 80 g/m² was used as a base material to press-bond it to the surface of the dry pressure sensitive adhesive layer, thereby obtaining a pressure sensitive adhesive tape. The pressure sensitive adhesive tape was further aged at 50° C. for 7 days to produce a medical pressure sensitive adhesive tape. This medical pressure sensitive adhesive tape was cut into pieces having a width of 24 mm to conduct various tests. The results thereof are shown in Table 1. This medical pressure sensitive adhesive tape exhibited far excellent performance in medical pressure sensitive adhesive tape in that skin irritation was extremely little at both edge and central portions of a site applied, and good holding and fixing function was exhibited even in the test for practical use.

Comparative Example 3

A solution of Pressure Sensitive Adhesive (C) was prepared in the same manner as in Example 3 except that no crosslinking agent was mixed. This pressure sensitive adhesive solution was applied to a separator having a thickness of 120 μm, one surface of which had been subjected to a silicone treatment, so as to give a dry coating thickness of 50 μm, and heated and dried at 120° C. for 5 minutes. A nonwoven rayon fabric was used as a base material to press-bond it to the surface of the dry pressure sensitive adhesive layer so as not to wrinkle, thereby obtaining a pressure sensitive adhesive tape. The pressure sensitive adhesive tape was further aged at 40° C. for 7 days to produce a medical pressure sensitive adhesive tape. This medical pressure sensitive adhesive tape was cut into pieces having a width of 24 mm to conduct various tests. The results thereof are shown in Table 1.

In this medical pressure sensitive adhesive tape, the water-vapor transmission rate of the pressure sensitive adhesive tape was 65 g/m²·24 hr because the moisture permeability of the pressure sensitive adhesive was poor due to its composition. In the case of Example 3, a treatment that the moisture permeability of the pressure sensitive adhesive is enhanced by bubbling the pressure sensitive adhesive was conducted. Therefore, contrastive results were obtained. With respect to the skin irritation, this medical pressure sensitive adhesive tape resulted in being strong at a central portion of a site applied and heavy at an edge portion. This was judged to be greatly attributed to a treatment that was conducted for removing the pressure sensitive adhesive remained on the skin upon peeling of the pressure sensitive adhesive tape due to small cohesive force of the pressure sensitive adhesive. In the test for practical use, the pressure sensitive adhesive remained on the applied site, and slippage occurred. This is considered to be due to insufficient cohesive force of the pressure sensitive adhesive, since the retention of the pressure sensitive adhesive was observed even in the measurement of the adhesive strength to human skin after 24 hours. When the logarithm of viscosity of the pressure sensitive adhesive is as small as 4.80, it is understood that the adhesive properties become poor.

Comparative Example 4

A solution of Pressure Sensitive Adhesive (C) was prepared in the same manner as in Example 3. This pressure sensitive adhesive solution was applied to a separator having a thickness of 120 μm, one surface of which had been subjected to a silicone treatment, so as to give a dry coating thickness of 50 μm, and heated and dried at 150° C. for 8 minutes. Minute bubbles were generated in the pressure sensitive adhesive by this treatment. A nonwoven rayon fabric was used as a base material to press-bond it to the surface of the dry pressure sensitive adhesive layer so as not to wrinkle, thereby obtaining a pressure sensitive adhesive tape. The pressure sensitive adhesive tape was further aged at 40° C. for 7 days to produce a medical pressure sensitive adhesive tape. This medical pressure sensitive adhesive tape was cut into pieces having a width of 24 mm to conduct various tests. The results thereof are shown in Table 1.

The medical pressure sensitive adhesive tape thus obtained was excellent in moisture permeability, adhesive strength to human skin and test for practical use. However, skin irritation was strong at both central and edge portions of a site applied due to too high stress at 5% elongation. In particular, skin irritation at the edge portion was heavy.

Comparative Example 5

A solution of Pressure Sensitive Adhesive (C) was prepared in the same manner as in Example 3. This pressure sensitive adhesive solution was applied to a separator having a thickness of 120 μm, one surface of which had been subjected to a silicone treatment, so as to give a dry coating thickness of 50 μm, and heated and dried at 120° C. for 5 minutes. An air-permeable polyolefin film having a thickness of 90 μm was used as a base material to press-bond it to the surface of the dry pressure sensitive adhesive layer, thereby obtaining a pressure sensitive adhesive tape. The pressure sensitive adhesive tape was further aged at 50° C. for 7 days to produce a medical pressure sensitive adhesive tape. This medical pressure sensitive adhesive tape was cut into pieces having a width of 24 mm to conduct various tests. The results thereof are shown in Table 1.

The medical pressure sensitive adhesive tape thus obtained was poor in moisture permeability, and in the test for practical use, partial separation or slippage was observed.

TABLE 1

| Item of properties | Unit | Ex. 1 | Comp. Ex. 1 | Ex. 2 | Comp. Ex. 2 | Ex. 3 | Comp. Ex. 3 | Comp. Ex. 4 | Comp. Ex. 5 |
|---|---|---|---|---|---|---|---|---|---|
| Base material | | Air-permeable polyolefin film | Polyethylene film | Knitted fabric of cotton yarn | Plain cotton fabric | Nonwoven urethane fabric | Nonwoven rayon fabric | Nonwoven rayon fabric | Air-permeable polyolefin film |
| Thickness of adhesive tape | | Acrylic (A) | Acrylic (A) | Acrylic (B) (bubbling) | Acrylic (B) | Acrylic (C) (bubbling) | Acrylic (C) | Acrylic (C) bubbling) | Acrylic (C) |
| Adhesive strength | μm | 130 | 170 | 400 | 240 | 300 | 116 | 115 | 131 |
| Adhesive strength to bakelite panel | N/24 mm | 1.5 | 1.1 | 7.7 | 8.8 | 8.37 | 3.7 | 3.2 | 2.3 |
| Logarithm of viscosity of adhesive | | 5.80 | 6.48 | 5.99 | 5.99 | 6.48 | 4.80 | 6.53 | 6.50 |
| Stress at 5% elongation of adhesive tape | N/24 mm | 7.1 | 13.6 | 0.32 | 160.8 | 1.59 | 27.6 | 27.4 | 7.2 |
| Water-vapor transmission rate | g/24 hr · m² | 1020 | 34 | 1110 | 89 | 6500 | 65 | 5742 | 105 |
| Adhesive strength to human skin | | | | | | | | | |
| Initial | N/24 mm | 0.69 | 1.2 | 2.2 | 1.5 | 1.9 | 1.5 | 1.7 | 1.1 |
| after 24 hr | N/24 mm | 0.66 | 0.2 | 2.6 | 0.85 | 3.2 | 2.70(*1) | 1.6 | 0.4 |
| Conductance | | | | | | | | | |
| Initial | μS | 9 | 12 | 8 | 13 | 13 | 12 | 13 | 12 |
| after 24 hr | μS | 30 | 620 | 21 | 542 | 18 | 127 | 18 | 280 |
| Skin irritation | | | | | | | | | |
| Center | | 13 | 13 | 13 | 38 | 6 | 31 | 31 | 13 |
| Edge | | 6 | 13 | 13 | 44 | 6 | 50 | 44 | 13 |
| Test for practical use | | ○ | X | ○ | ○ | ○ | X(*1) | ○ | Δ |

(Note)
(*1) The pressure sensitive adhesive remained.

INDUSTRIAL APPLICABILITY

According to the present invention, there are provided medical pressure sensitive adhesive tapes, by which skin irritation is greatly lightened, and the adhesive strength to skin is stably retained at a moderate level over a long period of time. In the medical pressure sensitive adhesive tapes according to the present invention, the conformability to skin, moisture permeability, tackiness to skin, etc. are all within respective moderate ranges, and these characteristics are balanced with one another at a high level. The medical pressure sensitive adhesive tapes according to the present invention are stable in the tackiness upon sweating or during sticking for a long period of time. In addition, the pain, corneum separation and skin irritation upon its peeling are lightened to a great extent.

What is claimed is:

1. A medical pressure sensitive adhesive tape comprising a base material and a pressure sensitive adhesive layer formed on at least one side of the base material, wherein the adhesive tape has the following characteristics:
   (a) the stress at 5% elongation being within a range of 0.1 to 8.0 N/24 mm as measured at a temperature of 23° C. and an extension rate of 100 mm/min;
   (b) the viscosity (unit: Pa·s) of a pressure sensitive adhesive being within a range of 5.0 to 6.7 in terms of logarithm as determined from an initial slippage under shear load; and
   (c) the water-vapor transmission rate being within a range of 800 to 8,000 g/m²·24 hr as measured at a temperature of 40° C. and a relative humidity of 90%.

2. The medical pressure sensitive adhesive tape according to claim 1, wherein the adhesive strength to bakelite panel is within a range of 0.6 to 10.0 N/24 mm.

3. The medical pressure sensitive adhesive tape according to claim 1, wherein the adhesive strength to human skin at an inner lower arm is within a range of 0.5 to 5.0 N/24 mm.

4. The medical pressure sensitive adhesive tape according to claim 1, wherein the pressure sensitive adhesive is a silicone pressure sensitive adhesive, rubber pressure sensitive adhesive, acrylic pressure sensitive adhesive or hydrogel pressure sensitive adhesive.

5. The medical pressure sensitive adhesive tape according to claim 4, wherein the pressure sensitive adhesive is an acrylic pressure sensitive adhesive.

6. The medical pressure sensitive adhesive tape according to claim 5, wherein the acrylic pressure sensitive adhesive is a copolymer of an alkyl (meth)acrylate with a functional monomer or vinyl ester monomer copolymerizable therewith, or a mixture of these monomers.

7. The medical pressure sensitive adhesive tape according to claim 5, wherein the acrylic pressure sensitive adhesive is a copolymer comprising (A) 50 to 97.5 wt. % of an alkyl (meth)acrylate having an alkyl group having 4 to 12 carbon atoms, (B) 2 to 49.5 wt. % of an alkoxypolyalkylene glycol (meth)acrylate, and (C) 0.5 to 15 wt. % of a hydroxyl group- or carboxyl group-containing monomer.

8. The medical pressure sensitive adhesive tape according to claim 7, wherein the alkoxypolyalkylene glycol (meth)acrylate is a (meth)acrylic ester represented by the formula (1):

wherein $R_1$ and $R_2$ are independently a hydrogen atom or a ethyl group, $R_3$ is an alkyl group having 1 to 20 carbon atoms, and n is an integer of 2 to 12.

9. The medical pressure sensitive adhesive tape according to claim 7, wherein the hydroxyl group-containing monomer is a hydroxyalkyl (meth)acrylate.

10. The medical pressure sensitive adhesive tape according to claim 7, wherein the carboxyl group-containing monomer is a carboxyalkyl (meth)acrylate.

11. The medical pressure sensitive adhesive tape according to claim 7, wherein the hydroxyl group-containing monomer is a hydroxyl group-containing (meth)acrylic ester represented by the formula (2):

wherein $R_4$ and $R_5$ are independently a hydrogen atom or a methyl group, and m is an integer of 2 to 12.

12. The medical pressure sensitive adhesive tape according to claim 7, wherein the carboxyl group-containing monomer is a carboxyl group-containing (meth)acrylic ester represented by the formula (3):

wherein $R_6$ is a hydrogen atom or a methyl group, and X is a divalent organic group having at least 2 carbon atoms and may contain a heteroatom such as an oxygen, nitrogen or sulfur atom.

13. The medical pressure sensitive adhesive tape according to claim 1, wherein the base material is a fabric, a nonwoven fabric, a film, a perforated film or a composite material thereof.

14. The medical pressure sensitive adhesive tape according to claim 13, wherein the film is a microporous, air-permeable film.

15. The medical pressure sensitive adhesive tape according to claim 1, wherein the pressure sensitive adhesive layer contains minute bubbles.

* * * * *